(12) United States Patent
Fukutsuka et al.

(10) Patent No.: US 11,857,360 B2
(45) Date of Patent: Jan. 2, 2024

(54) BIOLOGICAL SOUND MEASUREMENT DEVICE

(71) Applicant: OMRON HEALTHCARE Co., Ltd., Kyoto (JP)

(72) Inventors: Masayuki Fukutsuka, Kyoto (JP); Katsuyoshi Morita, Kyoto (JP); Kosuke Inoue, Kyoto (JP); Nobuki Yakura, Kyoto (JP); Seiji Fukunaga, Kyoto (JP); Tsuyoshi Ogihara, Kyoto (JP); Masahiko Yumoto, Kyoto (JP); Yuki Takuma, Kyoto (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 242 days.

(21) Appl. No.: 17/305,488

(22) Filed: Jul. 8, 2021

(65) Prior Publication Data

US 2021/0330280 A1 Oct. 28, 2021

Related U.S. Application Data

(63) Continuation of application No. PCT/JP2019/049679, filed on Dec. 18, 2019.

(30) Foreign Application Priority Data

Jan. 11, 2019 (JP) ................................ 2019-003484

(51) Int. Cl.
*A61B 7/04* (2006.01)
*A61B 5/00* (2006.01)
*H04R 1/46* (2006.01)

(52) U.S. Cl.
CPC .............. *A61B 7/04* (2013.01); *A61B 5/7445* (2013.01); *H04R 1/46* (2013.01); *A61B 2560/0425* (2013.01)

(58) Field of Classification Search
CPC . A61B 7/04; A61B 5/7445; A61B 2500/0425; H04R 1/46
See application file for complete search history.

(56) References Cited

U.S. PATENT DOCUMENTS

| 5,663,532 A | 9/1997 | Dieken et al. |
| 2005/0043642 A1* | 2/2005 | Sauerland ............ A61B 5/0002 600/528 |

(Continued)

FOREIGN PATENT DOCUMENTS

| CN | 105310714 A | 2/2016 |
| CN | 105769386 A | 7/2016 |

(Continued)

OTHER PUBLICATIONS

Written Opinion of the International Searching Authority, dated Feb. 10, 2020, for International Application No. PCT/JP2019/049679.

(Continued)

*Primary Examiner* — Andrew L Sniezek
(74) *Attorney, Agent, or Firm* — Birch, Stewart, Kolasch & Birch, LLP

(57) ABSTRACT

Provided is a biological sound measurement device capable of smoothly performing tasks from measurement initiation to result confirmation, that includes a sound measurement unit including a contact surface configured to be brought into contact with the body surface of a subject, a gripping portion supporting the sound measurement unit and configured to be gripped by a measurer, and a display unit provided to the gripping portion and configured to display an analysis result of a biological sound measured by the sound measurement unit. The gripping portion is configured to be gripped by the measurer in a state in which an index finger of the measurer is placed on a back surface of the sound measurement unit, and the display unit is provided on a (Continued)

surface of the gripping portion on the body surface side in a state in which the contact surface is in contact with the body surface.

4 Claims, 5 Drawing Sheets

(56) References Cited

U.S. PATENT DOCUMENTS

| | | | |
|---|---|---|---|
| 2008/0232604 | A1 | 9/2008 | Dufresne et al. |
| 2013/0131465 | A1 | 5/2013 | Yamamoto et al. |
| 2016/0296200 | A1 | 10/2016 | Hinojosa |
| 2018/0177482 | A1 | 6/2018 | Hashino et al. |
| 2018/0177485 | A1 | 6/2018 | Yakura et al. |
| 2018/0206736 | A1* | 7/2018 | Lee .................. A61B 5/02125 |

FOREIGN PATENT DOCUMENTS

| | | |
|---|---|---|
| CN | 105877775 A | 8/2016 |
| CN | 107693044 A | 2/2018 |
| DE | 7045017 U | 3/1971 |
| DE | 696 31 803 T2 | 1/2005 |
| DE | 10 2017 222 589 A1 | 6/2018 |
| DE | 10 2017 222 590 A1 | 6/2018 |
| JP | 2007-209609 A | 8/2007 |
| JP | 2010-522037 A | 7/2010 |
| JP | 2012-24391 A | 2/2012 |
| JP | 2016-158806 A | 9/2016 |
| JP | 2016-158807 A | 9/2016 |
| JP | 2017-60598 A | 3/2017 |
| JP | 2018-503493 A | 2/2018 |
| JP | 2018-102727 A | 7/2018 |
| WO | WO 2008/112693 A1 | 9/2008 |

OTHER PUBLICATIONS

German Office Action for German Application No. 11 2019 005 856.8, dated Jan. 25, 2023, with an English translation.

Chinese Office Action (including and English translation thereof) and Search Report issued in the corresponding Chinese Patent Application No. 201980082202.6 dated Nov. 2, 2023.

* cited by examiner

[FIG. 1]
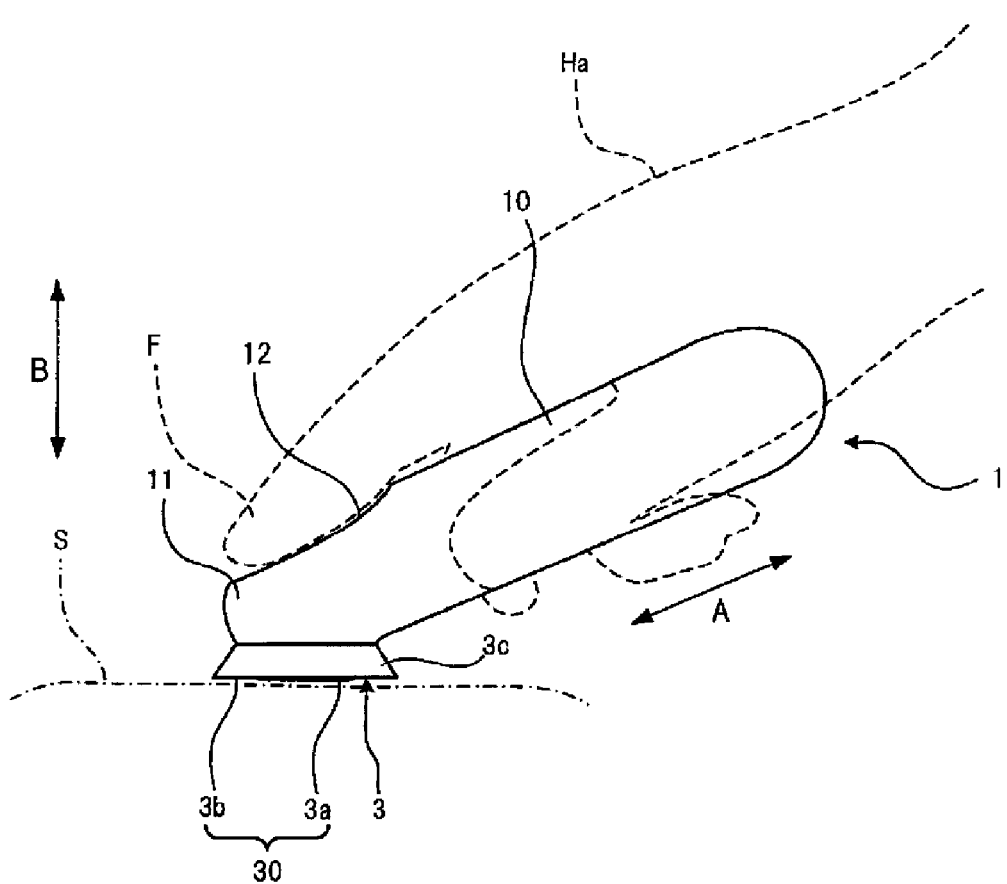

[FIG. 2]
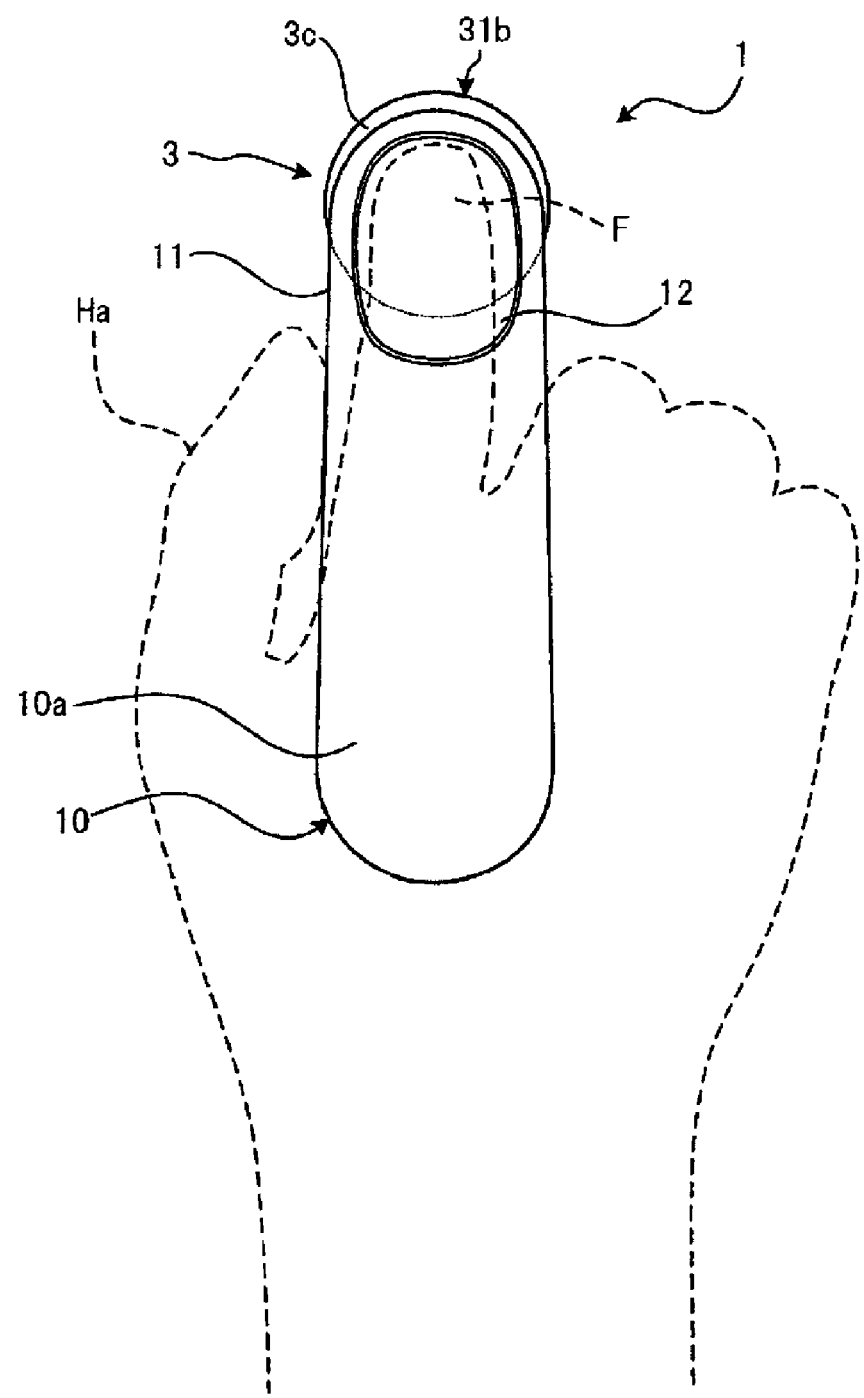

[FIG. 3]
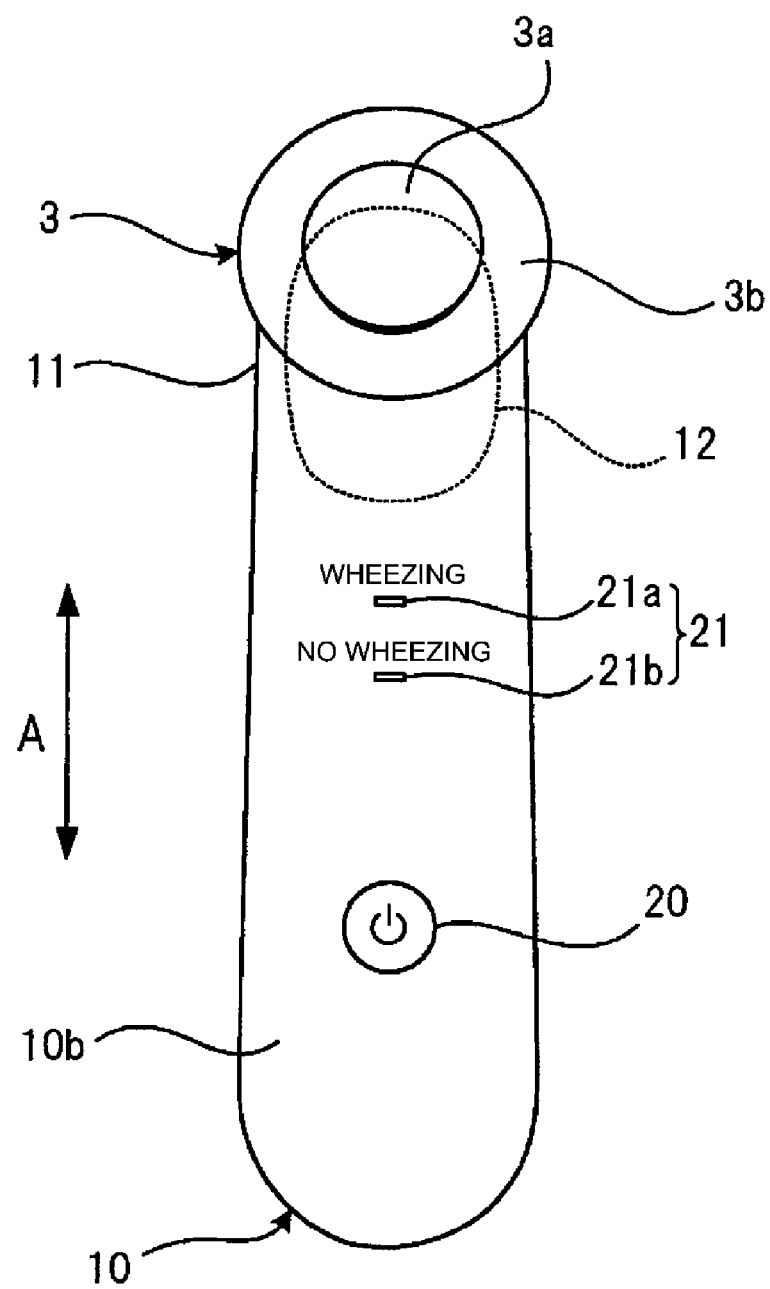

[FIG. 4]
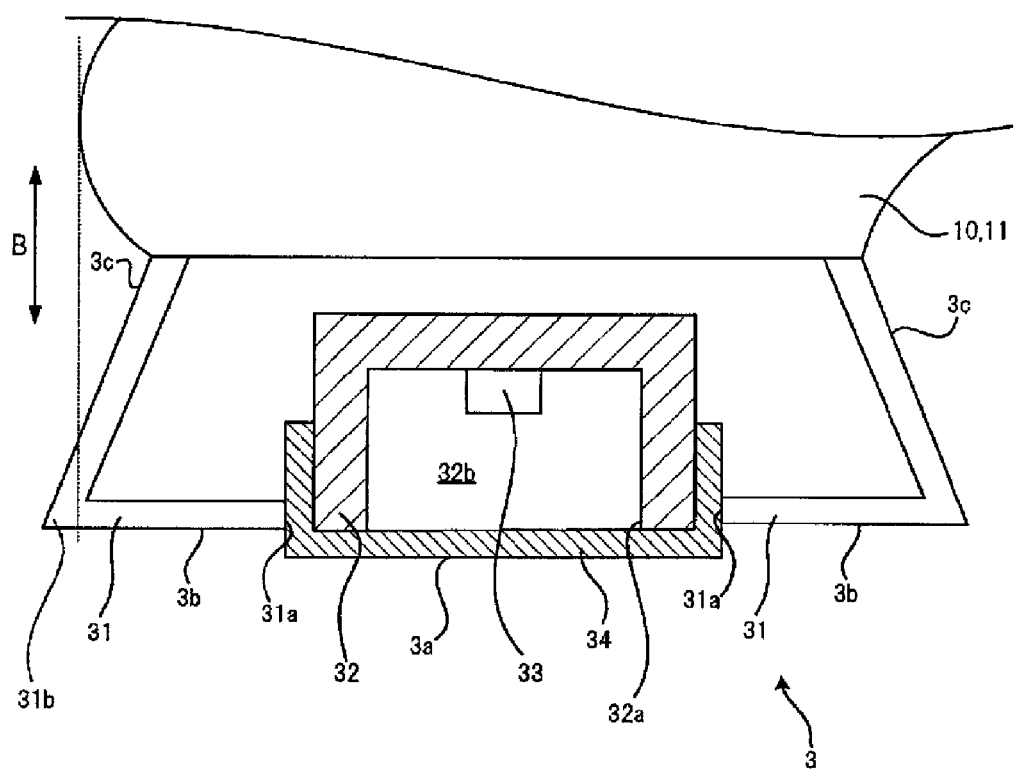

[FIG. 5]
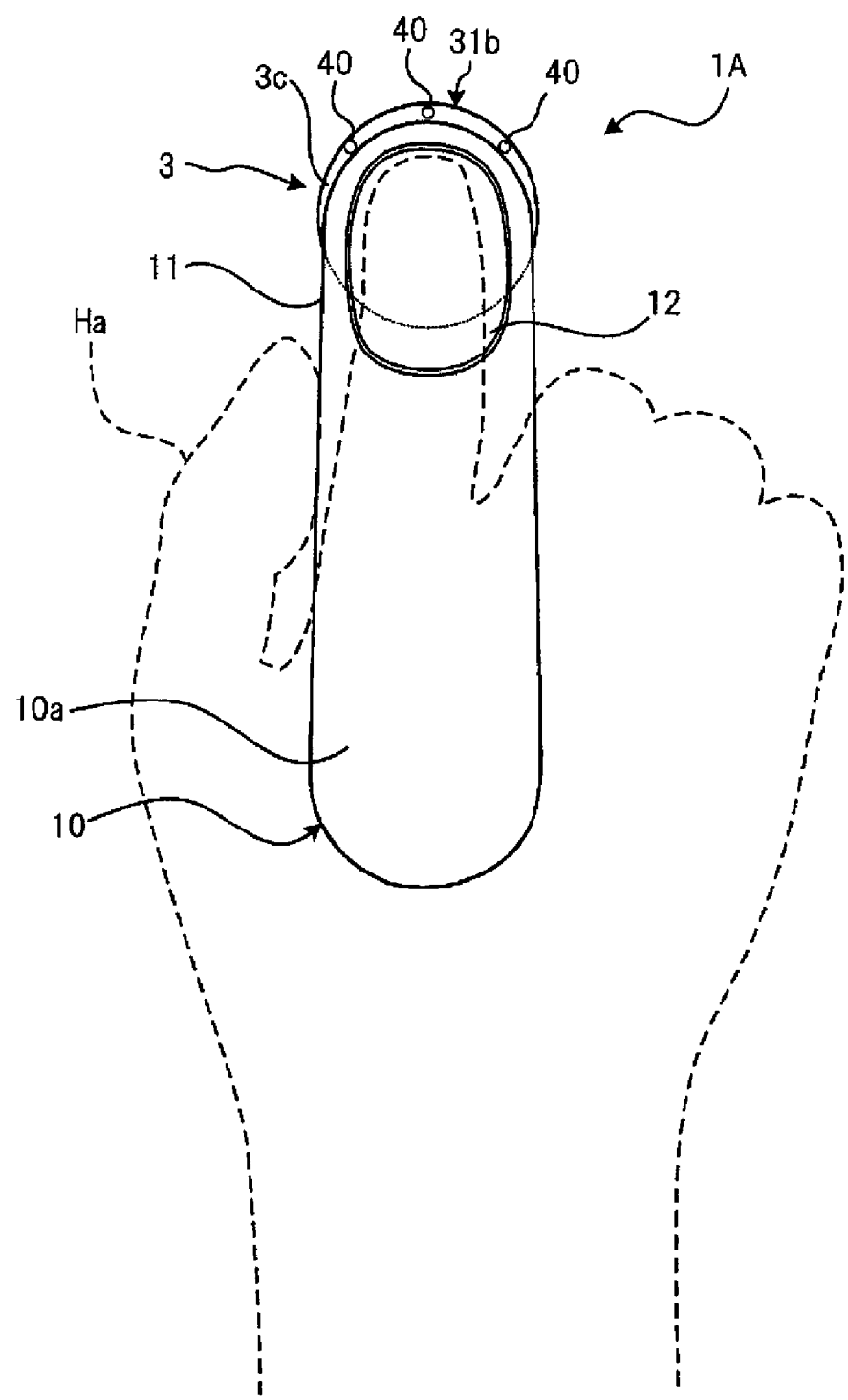

BIOLOGICAL SOUND MEASUREMENT DEVICE

CROSS-REFERENCE TO RELATED APPLICATIONS

This application is the U.S. national stage application filed pursuant to 35 U.S.C. 365(c) and 120 as a continuation of International Patent Application No. PCT/JP2019/049679, filed Dec. 18, 2019, which application claims priority to Japan Patent Application No. 2019-003484, filed Jan. 11, 2019, which applications are incorporated herein by reference in their entireties.

TECHNICAL FIELD

The present invention relates to a biological sound measurement device configured to be brought into contact with the body surface of a subject and measure a biological sound.

BACKGROUND ART

There are known devices configured to utilize a microphone or the like to pick up biological sounds including respiratory sounds, which are physiological sounds that originate from a flow of air generated in the respiratory tract by breathing, adventitious sounds, which are abnormal sounds generated under pathological conditions, such as wheezing or a pleural friction rub, heartbeat sounds that originate from the cardiovascular system, and the like as electrical signals (refer to, for example, Patent Document 1).

Patent Document 1 discloses a device capable of displaying a time transition of an occurrence frequency of wheezing of a person to be measured.

CITATION LIST

Patent Literature

Patent Document 1: JP 2016-158807 A

SUMMARY OF INVENTION

Technical Problem

In order to accurately measure a biological sound, it is necessary to bring a contact surface of the biological sound measurement device into contact with the body surface of a living body in an appropriate state. If the subject is an infant or the like, the subject may move frequently. Therefore, it is desirable that a measurer can focus on maintaining a contact state between the device and the body surface. Further, because the measurer needs to focus for a certain amount of time on maintaining the contact state between the device and the body surface, it is desirable to notify the measurer of a measurement result of the biological sound without imposing a burden on the measurer. Patent Document 1 does not recognize these problems.

In light of the foregoing, an object of the present invention is to provide a biological sound measurement device capable of smoothly performing tasks from measurement initiation to result confirmation.

Solution to Problem (1)

A biological sound measurement device configured to measure a biological sound of a subject includes a sound measurement unit including a contact surface configured to be brought into contact with the body surface of the subject, a gripping portion supporting the sound measurement unit and configured to be gripped by a measurer, and a display unit provided to the gripping portion and configured to display an analysis result of the biological sound measured by the sound measurement unit, wherein the gripping portion being configured to be gripped by the measurer in a state in which an index finger of the measurer is placed on a back surface of the sound measurement unit, and the display unit is provided on a surface of the gripping portion on the body surface side in a state in which the contact surface is in contact with the body surface.

According to (1), the display unit is not visible to the measurer while the biological sound is being measured by the sound measurement unit, making it possible for the measurer to focus on the measurement task. As a result, a measurement accuracy of the biological sound can be increased. Further, the analysis result of the biological sound is displayed on the display unit provided on the surface of the gripping portion on the body surface side, and thus the measurer can check the display unit without changing a gripping posture of the gripping portion. As a result, it is possible to smoothly perform tasks from initiation of the biological sound measurement task to confirmation of the analysis result and reduce the burden of the measurer.

(2)

The biological sound measurement device according to (1), wherein the display unit includes one or a plurality of light emitting elements and is configured to display the analysis result by changing a light emission position or a light emission color of the one or plurality of light emitting elements.

According to (2), it is possible to reduce the size of the gripping portion, reduce cost, and save energy. Further, for example, assuming that the device is utilized while an infant or the like is sleeping, the analysis result is displayed by slight light of the one or plurality of light emitting elements, making it possible to prevent the infant from being disturbed.

(3)

The biological sound measurement device according to (1) or (2) further includes an operation unit provided on the surface of the gripping portion on the body surface side in a state in which the contact surface is in contact with the body surface, the operation unit being configured to at least turn a power source on and off.

According to (3), the operation unit is in a position less likely to come into contact with a hand of the measurer during the biological sound measurement task. Thus, an occurrence of an erroneous operation during the measurement task can be prevented. Further, because the display unit and the operation unit are on the same surface, tasks such as operating the operation unit to turn off the power source, for example, after checking the display unit can be performed smoothly, making it possible to reduce the burden on the measurer.

(4)

The biological sound measurement device according to (3), wherein the display unit is provided between the sound measurement unit and the operation unit.

According to (4), the display unit is less likely to be hidden by a finger of the measurer, making it possible to more smoothly confirm the analysis result.

(5)

The biological sound measurement device according to any one of (1) to (4), wherein the gripping portion includes a recessed portion for placement of the index finger, and the display unit is provided adjacent to a region of the surface that overlaps the recessed portion in a state of viewing from a direction perpendicular to a longitudinal direction of the gripping portion.

According to (5), the display unit is less likely to be hidden by a finger of the measurer, making it possible to more smoothly confirm the analysis result.

Advantageous Effects of Invention

According to the present invention, it is possible to provide a biological sound measurement device capable of smoothly performing tasks from measurement initiation to result confirmation.

BRIEF DESCRIPTION OF DRAWINGS

FIG. 1 is a side view schematically illustrating an outline configuration of a biological sound measurement device 1, which is an embodiment of a biological sound measurement device according to the present invention.

FIG. 2 is a schematic view of the biological sound measurement device 1 illustrated in FIG. 1, viewed from a measurer side in a direction B.

FIG. 3 is a schematic view of the biological sound measurement device 1 illustrated in FIG. 2, viewed from a subject side.

FIG. 4 is a cross-sectional schematic view of a sound measurement unit 3 of the biological sound measurement device 1 illustrated in FIG. 1.

FIG. 5 is a diagram illustrating a configuration of a biologic sound measurement device 1A that is a modified example of the biological sound measurement device 1 of FIG. 1.

DESCRIPTION OF EMBODIMENTS

Overview of Biological Sound Measurement Device of Embodiment

First, an overview of an embodiment of a biological sound measurement device according to the present invention will be described. The biological sound measurement device according to the embodiment is configured to measure, as an example of a biological sound, a pulmonary sound from a subject such as a person and notify a measurer of an occurrence of wheezing when wheezing is determined to be included in the measured sound. In this way, it is possible to support the determination of the necessity of medication for the person to be measured, the determination of whether or not to take the person to the hospital, and the like.

The biological sound measurement device according to the embodiment includes a sound measurement unit including a contact surface configured to be brought into contact with the body surface of the subject such as a person, and a gripping portion supporting this sound measurement unit and configured to be gripped by a measurer. The gripping portion is provided with a display unit configured to display an analysis result of the biological sound measured by the sound measurement unit on a surface facing the body surface side in a state in which the sound measurement unit is in contact with the body surface of the subject.

With such a configuration, in a state in which the contact surface of the sound measurement unit has been brought into contact with the body surface, the display unit is in a state of not being visible to the measurer, making it possible for the measurer to focus on the measurement task and thus the measurement accuracy can be increased. Further, the operation from completion of the measurement task to confirmation of the analysis result can be performed smoothly, making it possible to reduce the burden on the measurer.

A specific configuration example of the biological sound measurement device according to the embodiment will be described below.

Embodiment

FIG. 1 is a side view schematically illustrating an outline configuration of a biological sound measurement device 1, which is an embodiment of the biological sound measurement device according to the present invention. FIG. 2 is a schematic view of the biological sound measurement device 1 illustrated in FIG. 1, viewed from the measurer side in a direction B. FIG. 3 is a schematic view of the biological sound measurement device 1 illustrated in FIG. 2, viewed from the subject side. FIG. 4 is a cross-sectional schematic view of a sound measurement unit 3 of the biological sound measurement device 1 illustrated in FIG. 1.

As illustrated in FIG. 1 to FIG. 3, the biological sound measurement device 1 includes a gripping portion 10 having a columnar shape extending in a direction A and constituted by a case of a resin, a metal, or the like. A head portion 11 is provided on one end side of this gripping portion 10. The gripping portion 10 is a portion gripped by the measurer.

An integrated control unit (not illustrated) configured to integrally control the entire biological sound measurement device 1, a battery (not illustrated) configured to supply a voltage required for operation, a display unit 21 illustrated in FIG. 3, and the like are provided inside the gripping portion 10.

The integrated control unit includes various processors, random access memory (RAM), read only memory (ROM), and the like, and performs a control and the like of each hardware of the biological sound measurement device 1 in accordance with a program.

As illustrated in FIG. 1 and FIG. 4, the head portion 11 is provided with the sound measurement unit 3 that protrudes toward one side (lower side in FIG. 1 and FIG. 4) in a direction intersecting the longitudinal direction A of the gripping portion 10. A contact surface 30 configured to be brought into contact with the body surface S of the subject is provided on a tip end of this sound measurement unit 3.

The contact surface 30 is constituted by a pressure-receiving region 3a (refer to FIG. 3) having a circular shape, for example, and an extended region 3b (refer to FIG. 3) having an annular shape, for example. The pressure-receiving region 3a is a flat surface required for receiving pressure from the body surface S, and the extended region 3b is a flat surface formed around the pressure-receiving region 3a and provided to increase a contact area with the body surface S. In the example of FIG. 1 and FIG. 4, the pressure-receiving region 3a protrudes slightly further toward the body surface S side than the extended region 3b, but may be formed on the same plane as the extended region 3b. The direction B illustrated in FIG. 1 is a direction perpendicular to the contact surface 30 and intersects the longitudinal direction A of the gripping portion 10.

As illustrated in FIG. 2, in a state of viewing in the direction B perpendicular to the contact surface 30, a recessed portion 12 for placement of an index finger F, for example, of a hand Ha of the measurer is formed on a surface 10a of the gripping portion 10, which is opposite side to the sound measurement unit 3 side, on a portion overlapping the sound measurement unit 3.

As illustrated in FIG. 1 and FIG. 2, the biological sound measurement device 1 is used, in a state in which the index finger F of the hand Ha of the measurer is placed in the recessed portion 12 of the gripping portion 10 and the gripping portion 10 is gripped by the hand Ha, with the contact surface 30 including the pressure-receiving region 3a of the sound measurement unit 3 being pressed against the body surface S by the index finger F.

As illustrated in FIG. 4, the sound measurement unit 3 includes the sound detector 33 such as a micro-electro-mechanical systems (MEMS) type microphone or a capacitive microphone, and a housing 32 having a bottomed tubular shape, forming an accommodation space 32b accommodating the sound detector 33, and including an opening 32a, a cover 34 closing the opening 32a from outside the accommodation space 32b and forming the pressure-receiving region 3a that receives pressure from the body surface S, and a case 31 supported by the gripping portion 10 and accommodating the housing 32 and the cover 34 in a state in which the cover 34 is exposed.

The housing 32 is made of a material having higher acoustic impedance than that of air and high rigidity, such as resin or metal. The housing 32 is preferably made of a material that reflects sound in a detection frequency band of the sound detector 33 in a sealed state of the housing 32 so that sound is not transmitted from the outside to the interior of the accommodation space 32b.

The cover 34 is a member having a bottomed tubular shape, and a shape of a hollow portion thereof substantially matches an outer wall shape of the housing 32. The cover 34 is made of a material having a flexibility, an acoustic impedance close to that of the human body, air, or water, and favorable biocompatibility. Examples of the material of the cover 34 include silicone and an elastomer.

The case 31 is made of resin, for example. The case 31 is formed with an opening 31a at an end portion of opposite side to the gripping portion 10 side, and a portion of the cover 34 is in a protruding and exposed state from this opening 31a. A front surface of the cover 34 exposed from this case 31 forms the pressure-receiving region 3a described above.

When the pressure-receiving region 3a is brought into close contact state with the body surface S, vibration of the body surface S generated by the pulmonary sound of the living body vibrates the cover 34. When the cover 34 vibrates, an internal pressure of the accommodation space 32b fluctuates due to this vibration and, by this internal pressure fluctuation, an electrical signal corresponding to the pulmonary sound is detected by the sound detector 33.

An outer surface of the portion of the case 31 protruding from the gripping portion 10 is constituted by the extended region 3b described above, which is formed of a flat surface having an annular shape, and a tapered surface 3c that connects an outer peripheral edge of the extended region 3b and the gripping portion 10. The tapered surface 3c is a surface having an outer diameter that continuously increases from the gripping portion 10 side toward the extended region 3b side.

As illustrated in FIG. 2, the sound measurement unit 3 and the gripping portion 10 partially overlap. In FIG. 2, a non-overlapping portion 31b of the sound measurement unit 3 positioned outside the gripping portion 10 includes the contact surface 30 described above. Then, a width of the non-overlapping portion 31b in a direction parallel to the contact surface 30 is greatest at a first position, which is a position of the contact surface 30 in the direction B (defined as the position of the extended region 3b). Further, at a position closer to the gripping portion 10 than the first position in the direction B, the width of the non-overlapping portion 31b in the direction parallel to the contact surface 30 is less than the width at the first position.

In other words, a cross-sectional area of a cross section of the non-overlapping portion 31b parallel to the contact surface 30 (area of the region surrounded by an outer edge of the non-overlapping portion 31b) is greatest at the first position and, at a position closer to the gripping portion 10 than the first position, is less than the cross-sectional area at the first position.

As illustrated in FIG. 3, the display unit 21 and an operation unit 20 are provided on a surface 10b of a front surface of the gripping portion 10 on the body surface S side in a state in which the contact surface 30 has been brought into contact with the body surface S.

The display unit 21 includes light emitting units 21a and 21b including light emitting elements such as light emitting diodes (LEDs). On the surface 10b of the gripping portion 10, the characters "Wheezing" are printed adjacent to an upper side of the light emitting unit 21a, and the characters "No wheezing" are printed adjacent to an upper side of the light emitting unit 21b.

The integrated control unit described above included in the gripping portion 10 notifies of a detection result of wheezing (analysis result of the biological sound) by the display unit 21. Specifically, in a case in which the integrated control unit analyzes the pulmonary sound detected by the sound detector 33 and, as a result, determines that wheezing is included in the pulmonary sound, the integrated control unit turns off the light emitting unit 21b and causes the light emitting unit 21a to emit light, thereby notifying the measurer that wheezing was detected. Further, in a case in which it is determined that wheezing is not included in the pulmonary sound, the integrated control unit turns off the light emitting unit 21a and causes the light emitting unit 21b to emit light, thereby notifying the measurer that wheezing was not detected. Note that only the light emitting unit 21a may be used as the display unit 21, and the integrated control unit may notify of the presence or absence of wheezing by changing the light emission color of the light emitting unit 21a in accordance with the measurement result.

As illustrated in FIG. 3, in the biological sound measurement device 1, in a state of viewing in a direction perpendicular to the longitudinal direction A of the gripping portion 10 (direction from the front to the back of the paper in FIG. 3), the display unit 21 is provided adjacent to a region of the surface 10b of the gripping portion 10 that overlaps the recessed portion 12, and the operation unit 20 is provided at a position on the surface 10b on the other end side of the gripping portion 10 from the display unit 21.

The operation unit 20 is an interface configured to perform various operations such as turning on a power source of the device, turning off the power source of the device, and initiating measurement of the biological sound. The operation unit 20 need only be configured to at least turn on and off the power source of the device. The operation unit 20 is constituted by a button or a switch capable of inputting an instruction by being pressed, or a sensor capable of inputting an instruction by being touched.

Effects of Biological Sound Measurement Device 1

As described above, according to the biological sound measurement device 1, the display unit 21 configured to display the analysis result of the biological sound is provided on the surface 10b of the gripping portion 10 on the body surface S side. That is, the display unit 21 is not visible to the measurer while the contact surface 30 is being brought into contact with the body surface S and the biological sound is being measured. Thus, the measurer can focus on measurement of the biological sound. Therefore, an event such as a change in the contact state between the contact surface 30 and the body surface S during measurement can be prevented, and the measurement accuracy of the biological sound can be ensured.

Further, according to the biological sound measurement device 1, the analysis result of the biological sound is displayed on the display unit 21 provided on the surface 10b of the gripping portion 10 on the body surface S side. Therefore, the measurer can check the display unit 21 without changing a gripping posture of the gripping portion 10. As a result, it is possible to smoothly perform tasks from initiation of the biological sound measurement task to confirmation of the analysis result and reduce the burden of the measurer.

Further, according to the biological sound measurement device 1, the display unit 21 is provided adjacent to the region of the surface 10b of the gripping portion 10 overlapping the recessed portion 12, in other words, in the vicinity of the sound measurement unit 3. Thus, even in a state in which the measurer is gripping the gripping portion 10 with the hand Ha, the display unit 21 is less likely to be hidden by the hand Ha. Accordingly, the analysis result can be confirmed more smoothly.

Further, according to the biological sound measurement device 1, the display unit 21 includes the one or plurality of light emitting elements and is configured to display the analysis result of the biological sound by changing a light emission position or a light emission color of the one or plurality of light emitting elements. Thus, it is possible to reduce a size of the gripping portion 10, reduce cost, and save energy. Further, for example, assuming that the biological sound measurement device 1 is utilized while an infant or the like is sleeping, the analysis result is displayed by slight light of the one or plurality of light emitting elements, making it possible to prevent the sleeping of the infant from being disturbed.

Further, according to the biological sound measurement device 1, the operation unit 20 is provided on the surface 10b of the gripping portion 10 on the body surface S side. Thus, while the contact surface 30 is being brought into contact with the body surface S and the biological sound is being measured, a finger of the measurer is less likely to touch the operation unit 20, and erroneous operation during measurement can be prevented. Further, after measurement is completed, the measurer can check the display unit 21 and subsequently operate the operation unit 20 with a thumb, for example, and turn off the power source as is. In this way, the tasks from confirmation of the measurement result to turning the power source off can be performed smoothly and convenience can be improved.

Further, according to the biological sound measurement device 1, in a state in which the contact surface 30 of the sound measurement unit 3 is in contact with the body surface S, the outer edge of the non-overlapping portion 31b not overlapping the gripping portion 10 of the sound measurement unit 3 becomes the outer edge of the contact surface 30 as is, and is visible. Therefore, the contact state between the contact surface 30 and the body surface S can be easily confirmed. As a result, a favorable contact state can be easily achieved, making it possible to improve the measurement accuracy of the biological sound.

Further, according to the biological sound measurement device 1, the side surface of the sound measurement unit 3 excluding the contact surface 30 of the case 31 is the tapered surface 3c that decreases in diameter (width) from the contact surface 30 toward the gripping portion 10. This makes it possible to secure space for avoiding interference with clothing, a bone, and the like between the tapered surface 3c and the gripping portion 10 while increasing the area of the contact surface 30 to enable stable contact with the body surface S. As a result, preparatory work prior to the start of measurement of the biological sound can be performed smoothly. In particular, in a device configured to detect wheezing from a pulmonary sound, the subject is presumably an infant or the like. An infant presumably moves frequently and thus, with this work being performed smoothly, the burden on the measurer can be alleviated.

Further, according to the biological sound measurement device 1, the longitudinal direction (direction A) of the gripping portion 10 and the contact surface 30 intersect. Thus, in a state in which the contact surface 30 is in contact with the body surface S, the gripping portion 10 is not parallel to the body surface S. In such a configuration, the outer edge of the non-overlapping portion 31b becomes visible as an outer edge of the contact surface 30 as is and, regardless of the orientation of the gripping portion 10, the contact state between the contact surface 30 and the body surface S can be intuitively determined. As a result, it is possible to improve the measurement accuracy of the biological sound while alleviating the burden on the measurer.

Modified Example of Biological Sound Measurement Device 1

FIG. 5 is a diagram illustrating a configuration of a biologic sound measurement device 1A that is a modified example of the biological sound measurement device 1 of FIG. 1, and corresponds to FIG. 2. The biological sound measurement device 1A has the same configuration as that of the biological sound measurement device 1 except that three light emitting units 40 are added to the non-overlapping portion 31b.

The light emitting units 40 are configured to emit light by light emitting elements such as LEDs, and are embedded in the case 31, for example, in a partially exposed state. The light emitting units 40 are controlled by the integrated control unit.

For example, the integrated control unit determines a state of close contact between the contact surface 30 and the body surface S and, in a case in which it is determined that the state of close contact is not suitable for measurement of the biological sound, causes light to be emitted from the light emitting units 40. Alternatively, to notify the measurer that measurement is in progress while the biological sound is being measured, the integrated control unit performs control that causes the three light emitting units 40 to sequentially emit light in a predetermined pattern. As the measurement process of the biological sound progresses, the integrated control unit may perform control that increases the number of light emitting units 40 that emit light.

Thus, because the light emitting units 40 are located in the non-overlapping portion 31b to be visible to the measurer even in a state in which the contact surface 30 has been brought into contact with the body surface S, even if the biological sound measurement device 1A is largely hidden by the hand Ha as illustrated in FIG. 5, the measurer can be notified of various notifications other than the analysis result to the measurer. In the biological sound measurement device 1A, the display unit 21 provided on the surface 10b displays the analysis result and the light emitting units 40 indicate notifications to the measurer during measurement of the biological sound, thereby allowing the measurer to smoothly confirm the measurement result while focusing on the measurement task to improve measurement accuracy.

Note that the number of the light emitting units 40 included in the biological sound measurement device 1A is not limited to three, and may be one, two, or four or more.

Other Modified Examples

The display unit 21 may be any unit as long as capable of notifying the measurer of the analysis result of the biological sound, and may display the analysis result as an image by, for example, an organic electro-luminescence (EL) panel or a liquid crystal display panel.

The positions of the display unit 21 and the operation unit 20 may be reversed. Further, it is sufficient to provide at least the display unit 21 on the surface 10b, and the operation unit 20 may be provided on the surface 10a, for example.

In the biological sound measurement devices 1 and 1A, the longitudinal direction (direction A) of the gripping portion 10 and the contact surface 30 may be configured to be parallel. Further, the side surface of the case 31 may be a surface parallel to the direction B, for example, rather than the tapered surface 3c. Further, the sound measurement unit 3 may be configured to be completely concealed by the gripping portion 10 (configured without the non-overlapping portion 31b) in a state of viewing from the direction B.

While various embodiments have been described with reference to the drawings, needless to say, the present invention is not limited to such examples. It will be apparent to those skilled in the art that various changes and modifications can be made within the scope of the claims, and it is understood that these are naturally belong within the technical scope of the present invention. Further, each of the components of the above-described embodiments may be combined as desired within a range that does not depart from the spirit of the present invention.

Note that the present application is based on Japanese Patent Application filed Jan. 11, 2019 (JP 2019-3484), the contents of which are incorporated herein by reference.

REFERENCE SIGNS LIST 1, 1A Biological sound measurement device
3 Sound measurement unit
10 Gripping portion
10a, 10b Surface
11 Head portion
12 Recessed portion
3a Pressure-receiving region
3b Extended region
3c Tapered surface
30 Contact surface
31 Case
31a, 32a Opening
31b Non-overlapping portion
32 Housing
32b Accommodation space
33 Sound detector
34 Cover
20 Operation unit
21 Display unit
21a, 21b, 40 Light emitting unit
S Body surface
Ha Hand
F Index finger

The invention claimed is:

1. A biological sound measurement device configured to measure a biological sound of a subject, comprising:
a sound measurement unit including a contact surface configured to be brought into contact with a body surface of the subject;
a gripping portion supporting the sound measurement unit and configured to be gripped by a measurer;
a display unit provided to the gripping portion and configured to display an analysis result of the biological sound measured by the sound measurement unit; and
an operation unit being configured to at least turn a power source on and off, wherein
the gripping portion being configured to be gripped by the measurer in a state in which an index finger of the measurer is placed on a back surface of the sound measurement unit,
the display unit and the operation unit are provided on a surface of the gripping portion facing to the body surface in a state in which the contact surface is in contact with the body surface, and
a head portion is provided on one end side of the gripping portion, and the head portion is provided with the sound measurement unit that protrudes toward one side in a direction intersecting a longitudinal direction of the gripping portion.

2. The biological sound measurement device according to claim 1, wherein the display unit includes one or a plurality of light emitting elements and is configured to display the analysis result by changing a light emission position or a light emission color of the one or plurality of light emitting elements.

3. The biological sound measurement device according to claim 1, wherein the display unit is provided between the sound measurement unit and the operation unit disposed on the surface of the gripping portion facing to the body surface in the state in which the contact surface is in contact with the body surface.

4. The biological sound measurement device according to claim 1, wherein the gripping portion comprises a recessed portion for placement of the index finger, the recessed portion being provided on the back surface of the sound measurement unit, and
the display unit is provided at a portion of the surface of the gripping portion facing to the body surface in the state in which the contact surface is in contact with the body surface, so that the portion of the surface of the gripping portion, on which the display unit is provided, is adjacent to a region of the surface of the gripping portion facing to the body surface in the state in which the contact surface is in contact with the body surface, the region overlapping the recessed portion in a state of viewing from a direction perpendicular to the longitudinal direction of the gripping portion.

* * * * *